US00PP16431P2

(12) United States Plant Patent
Whetman

(10) Patent No.: US PP16,431 P2
(45) Date of Patent: Apr. 11, 2006

(54) ***DIANTHUS* PLANT NAMED 'DEVON STARLING'**

(50) Latin Name: *Dianthus×hybrida*
Varietal Denomination: Devon Starling

(76) Inventor: John Whetman, Deer Park Farm, Newton Abbot Devon Chudleigh TQ13 0NH (GB)

( * ) Notice: Subject to any disclaimer, the term of this patent is extended or adjusted under 35 U.S.C. 154(b) by 123 days.

(21) Appl. No.: 10/888,924

(22) Filed: Jul. 12, 2004

(51) Int. Cl.
*A01H 5/00* (2006.01)

(52) U.S. Cl. ..... Plt./273

(58) Field of Classification Search ..... Plt./273, Plt./272, 277, 276, 282
See application file for complete search history.

*Primary Examiner*—Anne Marie Grunberg
*Assistant Examiner*—June Hwu

(57) ABSTRACT

A new cultivar of *Dianthus* plant named 'Devon Starling' that is characterized by pronounced compact habit, grey-green foliage, and vivid purple flowers. In combination these traits set 'Devon Starling' apart from all other existing varieties of *Dianthus* known to the inventor.

2 Drawing Sheets

Genus: *Dianthus.*
Species: ×*hybrida.*
Denomination: Devon Starling.

BACKGROUND OF THE INVENTION

The present invention relates to a new and distinct cultivar of carnation that is grown for use as a flowering plant for pots and containers. The new cultivar is known botanically as *Dianthus×hybrida* and will be referred to hereinafter by the cultivar name 'Devon Starling'.

'Devon Starling' is a complex hybrid plant that is the product of a breeding program started by the inventor in 1980. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'Devon Starling' in 2000 for its unique pronounced compact habit accompanied by abundant vivid purple flowers that bloom from May through October.

'Devon Starling' is a dwarf carnation exhibiting pronounced compact habit, grey-green foliage, and vivid purple flowers. The colors of stems, leaves, calyx, and epicalyx are of material retaining the characteristic waxy bloom of *Dianthus*. 'Devon Starling' resulted from the open pollination between *Dianthus* 'Peace' (unpatented) as female parent plant and an unidentified and unknown variety of *Dianthus* as male parent plant. *Dianthus* 'Peace' is a cultivar of unknown parentage but derived from *Dianthus gratianopolitanus* (species, unpatented) and other *Dianthus* species and hybrids.

'Devon Starling' is distinguishable from the female parent by pronounced compact habit and purple flowers. *Dianthus gratianopolitanus*, also known as the Cheddar Pink, has pink flowers on a loose open plant habit.

The varieties of *Dianthus* which are considered by the inventor to most closely resemble 'Devon Starling' are the two unpatented varieties *Dianthus* 'Whatfield Magenta' and *Dianthus* 'Warden Hybrid'. When compared with these two varieties, the flowers of 'Devon Starling' are larger and exhibit a deeper and more saturated coloration. In addition, plants of 'Devon Starling' flower over a longer period than the two varieties and the plant habit of 'Devon Starling' is more compact and mounding.

Asexual reproduction of the new cultivar was first accomplished by the inventor in 2000 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'Devon Starling'. These traits in combination distinguish this cultivar from all other commercial varieties known to the inventor. 'Devon Starling' has not been tested under all possible conditions and phenotypic differences may be observed with variations in environmental, climatic and cultural conditions, however, without any variance in genotype.

1. *Dianthus* 'Devon Starling' exhibits a prononced compact habit.
2. *Dianthus* 'Devon Starling' blooms profusely.
3. *Dianthus* 'Devon Starling' exhibits vivid purple flowers from May through October.
4. *Dianthus* 'Devon Starling' exhibits grey-green foliage.
5. At maturity, the height of the foliage mound of *Dianthus* 'Devon Starling' is 100 mm; or 120 mm including flowers. The mature width is approximately 300 mm.
6. *Dianthus* 'Devon Starling' is a perennial herb.
7. *Dianthus* 'Devon Starling' is suitable for use as a flowering plant in pots and containers.
8. *Dianthus* 'Devon Starling' is hardy to minus 15° Centigrade.

BRIEF DESCRIPTION OF THE DRAWINGS

The accompanying color drawings illustrate the overall appearance of the new *Dianthus* variety 'Devon Starling' showing colors as true as it is reasonably possible to obtain in colored reproductions of this type. Colors in the drawings may differ from the color values cited in the detailed botanical description, which accurately describe the actual colors of the new variety 'Devon Starling'.

The drawing labeled as FIG. 1 depicts an entire flowering plant.

Figure 1:
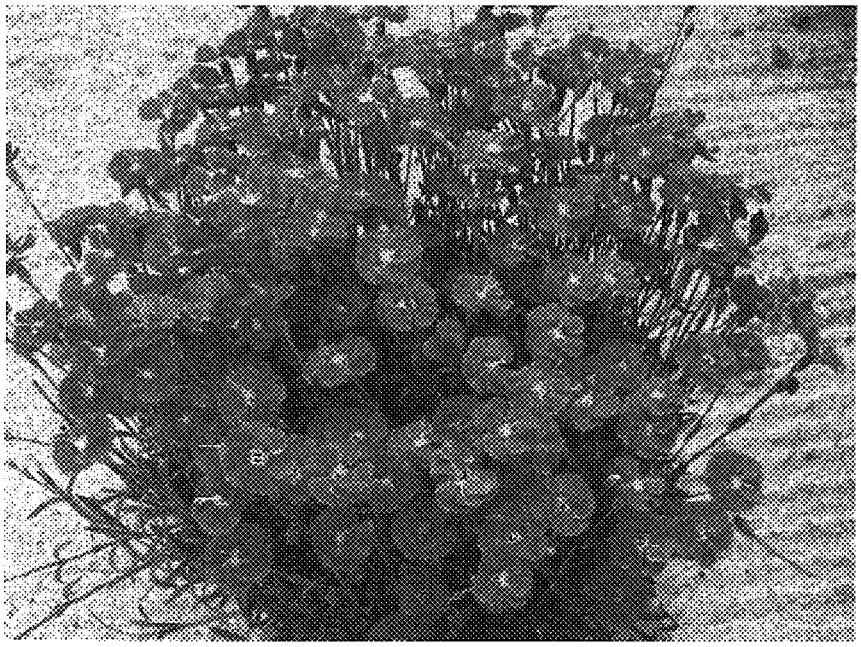
Figure 2:
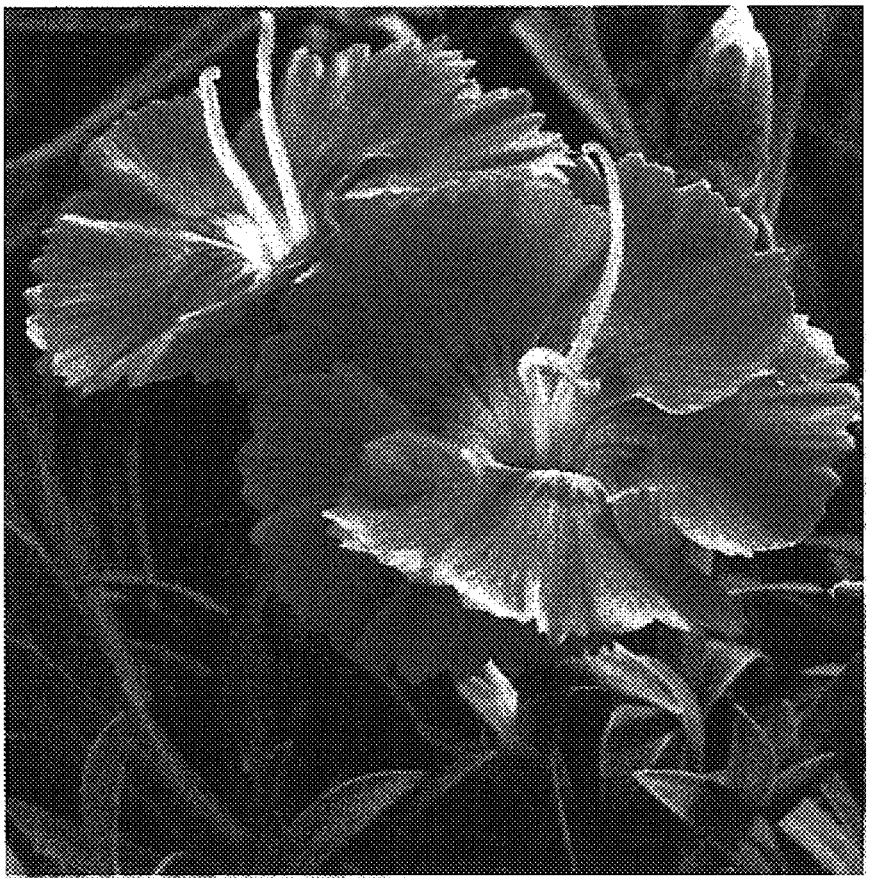

The drawing labeled as FIG. 2 depicts a close-up view of the flower.

All drawings were made of plants grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Starling'. Data was collected in spring from 1.5-liter container plants in spring, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus* 'Devon Starling'.
Species: ×*hybrida*.
Common name: Dwarf carnation.
Commercial classification: *Dianthus* hybrid.
Type: Perennial herb.
Use: Used as a flowering plant for pots and containers.
Parentage: 'Devon Starling' is a complex hybrid plant that resulted from the induced open pollination between the following parent plants:
- *Female parent plant.*—*Dianthus* 'Peace', itself derived from *Dianthus gratianopolitanus* (species).
- *Male parent plant.*—Unidentified *Dianthus* hybrid.

Plant description:
- *Bloom period.*—May through October.
- *Plant habit.*—Pronounced compact habit.
- *Plant height.*—120 mm. in height at maturity, including flower stalks.
- *Plant width.*—300 mm. in width at maturity.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun, with moderate water, and well-drained moderately fertile soil.
- *Diseases and pests.*—Susceptible to known *Dianthus* pests and disease but no other susceptibilities to pests or disease are known to the inventor.
- *Time and temperature needed to produce a rooted cutting.*—2 weeks are needed to produce roots on cuttings using a mist propagation unit with bottom heat of 20° Centigrade, and a minimum air temperature of 15° Centigrade.
- *Crop time.*—An average of 5 months is needed to produce a finished container size plant from a well-rooted cutting.

Stem:
- *Shape.*—Cylindrical.
- *Stem dimensions.*—75–100 mm. in length and 2 mm. in diameter.
- *Stem surface.*—Glabrous and glaucous.
- *Stem color.*—145C.
- *Branching.*—Numerous basal breaks.
- *Internode length.*—3–4 mm. between nodes.
- *Node color.*—145D.
- *Node dimensions.*—4 mm. in diameter and 3 mm. in length.

Foliage:
- *Type.*—Evergreen.
- *Shape.*—Lanceolate.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—35 mm. in length and an average of 4 mm. in width.
- *Leaf color* (*adaxial surfaces*).—N138A.
- *Leaf color* (*abaxial surfaces*).—N138C.
- *Fragrance.*—Absent.

Flowers:
- *Inflorescence.*—Raceme.
- *Number of flowers per stem.*—From 1 to 5.
- *Flower type.*—Salviform, single and symmetrical.
- *Flower length* (*pedicel, including calyx*).—30 mm–35 mm.
- *Flower diameter.*—20 mm–25 mm.
- *Fragrance.*—Present, mildly clove-like.
- *Bud color.*—N138C.
- *Anthocyanin.*—When present, pigmentation varies between 79A and 79B and between N79A and N79D.
- *Bud dimensions.*—20 mm. in length and 6 mm. in width.
- *Bud shape.*—Cylindrical.
- *Petals.*—Persistent, apopetalous, overlapping.
- *Petal number.*—Five petals.
- *Petal margin.*—Slightly dentate (toothed 1 mm deep).
- *Petal shape.*—Obdeltoid and slightly folded.
- *Petal surface.*—Glabrous.
- *Petal dimensions.*—30 mm. in length and 25 mm. in width.
- *Petal color* (*adaxial surface*).—Petal consists of rounded blade with strap-like base. Outermost two-thirds band of blade: Color varies between N74B and N74C. Band at widest section of blade (forms ring with other petals): N74A. Lowest (nearest center of flower) band of blade: N74C suffusing to N74D. Where band narrows sharply to strap-like base: N74D. Strap: Varies from N74D through 145A to 145D at lowest (nearest center of flower) point. Thus, flower adaxial surface presents a ring of more saturated purple, N74A, and the effect of an eye which is formed by the lower petal straps, colored 145A. Eye appears white in comparison with the saturated purple color of the blades which surround the eye.

*Petal color* (*abaxial surface*).—Whole of blade: N74C (that is, no ring present). Strap-like base: Ranges from 145A (outermost) to 145D (innermost).

*Calyx dimensions.*—7 mm. in diameter and 15 mm in length.

*Calyx color.*—N138C.

*Anthocynanin.*—When present, pigmentation varies between 79A and 79B and between N79A and N79D.

*Sepals.*—Five in number.

*Fused or unfused.*—Sepals fused.

*Sepal color.*—N138C.

*Anthocyanin.*—When present, pigmentation varies between 79A and 79B and between N79A and N79D.

*Peduncle dimensions.*—120 mm–150 mm. in length and 2 mm. in diameter.

*Peduncle color.*—N138C.

*Peduncle surface.*—Glaucous.

*Epicalyx.*—Present, consisting of two pairs of bracts.

*Bracts.*—Two pairs in number (4 individual bracts).

*Bract dimensions.*—Upper pair are 8 mm. in width and 6 mm. in length. Lower pair are 8 mm. in width and 8 mm. in length.

*Bract color* (*upper and lower pair*).—Colors N138A and 145C are individually present on individual bracts.

*Anthocyanin.*—When present, pigmentation varies between 79A and 79B and between N79A and N79D.

*Stipules.*—Two per node.

*Stipule dimensions.*—A range of 3–5 mm. in width and a range of 7–35 mm. in length.

*Stipule color.*—139C.

*Anthocyanin.*—Present.

*Lastingness of flower.*—Each individual flower lasts an average of 10 days at 20° Centigrade.

Reproductive organs:

*Stamens.*—From 0 to 15 stamens may be present on an individual flower.

*Stamen dimensions.*—3 mm. in length and 1 mm. in diameter.

*Stamen color.*—N74D.

*Anther number.*—Number of anthers range from none if stamens are absent on flower, to many, according to the number of stamens present on an individual flower.

*Anther attachment.*—Dorsifixed.

*Anther color.*—N74D.

*Anther dimensions.*—3 mm. in length and 1 mm. in diameter.

*Pollen.*—Present if anthers are present.

*Amount of pollen.*—When present the amount is moderate.

*Pollen color.*—When pollen is present the color ranges from 155A to N74D.

*Pistil.*—One that divides into two above the ovary.

*Pistil dimensions.*—37 mm. in length.

*Styles.*—Two in number.

*Style dimensions.*—20 mm. in length and 1 mm. in diameter.

*Style color.*—Colors 155A and N74D are individually present on the individual styles.

*Stigma number.*—Two in number.

*Stigma shape.*—A single stigma that can be trifid or bifid on an individual flower.

*Color of stigma.*—N74D.

*Height above petals.*—10 mm. above petals.

*Ovary position.*—Superior.

*Ovary dimensions.*—7 mm. in length and 5 mm. in diameter.

*Ovary shape.*—Spindle shaped.

*Ovary color.*—Colors 141C and 144C are individually present on an individual ovary.

Seed:

*Seed.*—Present.

*Seed dimensions.*—2 mm. in length and 1 mm. in width.

*Color.*—Color of seed that results from an individual flower ranges from 202A to 202B.

I claim:

1. A new and distinct cultivar of *Dianthus* plant named 'Devon Starling' as described and illustrated herein.

* * * * *